(12) United States Patent
Peszynski

(10) Patent No.: US 7,588,536 B2
(45) Date of Patent: Sep. 15, 2009

(54) CONTROL MECHANISM FOR AN ENDOSCOPE

(75) Inventor: Michael Peszynski, Newburyport, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 539 days.

(21) Appl. No.: 10/530,619

(22) PCT Filed: Sep. 8, 2003

(86) PCT No.: PCT/IB03/03947

§ 371 (c)(1), (2), (4) Date: Apr. 7, 2005

(87) PCT Pub. No.: WO2004/032730

PCT Pub. Date: Apr. 22, 2004

(65) Prior Publication Data

US 2006/0167343 A1    Jul. 27, 2006

Related U.S. Application Data

(60) Provisional application No. 60/417,835, filed on Oct. 11, 2002, provisional application No. 60/485,771, filed on Jul. 9, 2003.

(51) Int. Cl.
*A61B 1/00* (2006.01)
(52) U.S. Cl. .................. 600/146; 600/144; 600/147
(58) Field of Classification Search ................ 600/129, 600/137, 139, 144, 146, 149, 106, 131, 147
See application file for complete search history.

(56) References Cited

U.S. PATENT DOCUMENTS

| | | | |
|---|---|---|---|
| 3,788,303 A * | 1/1974 | Hall | 600/148 |
| 4,207,873 A | 6/1980 | Kruy | |
| 4,461,282 A | 7/1984 | Ouchi et al. | |
| 4,534,339 A | 8/1985 | Collins et al. | |
| 4,825,850 A * | 5/1989 | Opie et al. | 600/122 |
| 5,388,568 A * | 2/1995 | van der Heide | 600/146 |
| 5,464,007 A | 11/1995 | Krauter et al. | |
| 5,479,930 A | 1/1996 | Gruner et al. | |
| 5,575,755 A | 11/1996 | Krauter et al. | |
| 5,738,631 A | 4/1998 | Konstorum | |
| 5,762,067 A | 6/1998 | Dunham et al. | |
| 2003/0219184 A1 * | 11/2003 | Rio | 384/523 |

* cited by examiner

*Primary Examiner*—Linda C Dvorak
*Assistant Examiner*—Alireza Nia

(57) ABSTRACT

Control mechanism (10) for an endoscope including first and second independently rotatable control knobs (18,20), an inner pinion shaft (22) fixed to the first control knob (18), an outer pinion shaft (28) fixed to the second control knob (20) and coaxial with the inner shaft (22) and an intermediate shaft (34) arranged at least partially inside of the outer shaft (28) and at least partially around the inner shaft (22). O-rings (42,46) between the intermediate shaft (34) and the inner and outer shafts (22,28) seal the interior of the endoscope and transfer torque from the inner or outer shaft (22,28) to the intermediate shaft (34), which is grounded against rotation and therefore does not transfer torque to the other shaft (22, 28). A non-cross-coupling control mechanism is achieved in which the rotation of one control knob and its associated shaft does not have any effect on the other control knob and associated shaft.

21 Claims, 3 Drawing Sheets

CONTROL MECHANISM FOR AN ENDOSCOPE

CROSS REFERENCE TO RELATED CASES

Applicant claims the benefit of Provisional Application Ser. No. 60/417,835, filed Oct. 11, 2002, and Provisional Application Ser. No. 60/485,771, filed Jul. 9, 2003.

The present invention relates generally to control mechanisms for medical instruments designed to inspect internal organs and other structure in a body and more particularly to control mechanisms for endoscopes usable for transesophageal echocardiogram (TEE) imaging.

Various medical instruments are designed to be inserted into a human body to inspect or image internal organs and other structures in the body. Endoscopes are one form of such instruments and typically include a handle and a flexible shaft extending from the handle and having a distal or operative end which is inserted into the body through a body cavity such as the mouth. The distal end of the shaft includes an optical bundle or CCD array, or another type of image-receiving sensor.

To enable the distal end of the shaft to be capable of controlled adjustable movement, endoscopic flexible links are arranged at the distal end of the shaft and connect to cables or wires arranged in the shaft and which are mechanically coupled to knobs on the handle. As such, the links, and thus the distal end of the shaft, can be moved in a controlled manner by manual adjustment of the knobs.

Typically, there are two pairs of cables arranged in the shaft, one pair for flexing the distal end of the shaft in one plane and the other pair for flexing the distal end of the shaft in a perpendicular plane. Two independently rotatable knobs are arranged on the handle and mounted concentrically one on top of the other to provide for a compact design. An uppermost one of the knobs is coupled to a pair of racks lying in a common plane via an inner shaft having a pinion engaging with the racks and a lowermost knob is linked to another pair of racks lying in another common plane via an outer shaft having a pinion engaging with those racks. The outer shaft is arranged directly around the inner shaft and is coaxial therewith.

Each pinion is situated between the respective associated pair of racks, i.e., the racks are on opposite sides of the pinion so that the direction of movement of one rack is opposite to the direction of movement of the other rack. Rotation of one of the knobs causes rotation of its associated shaft and pinion and thus lateral movement of the racks engaging with the pinion. Since one of the racks is moved in one direction while the other rack is moved in the opposite direction, one cable is pulled and other pushed thereby causing the distal end of the shaft to turn. Adjustment of the distal end of the shaft in any direction is thereby enabled by rotating the knobs.

Prior art endoscopes having the above structure are described, for example, in U.S. Pat. Nos. 4,534,339. 5,479,930 and 5,762,067 describe similar endoscopes but instead of a rack and pinion movement transmission mechanism, a pulley and cable transmission mechanism is used.

A problem with the prior art endoscopes of this type is that as one knob and its associated shaft are rotated to cause movement of the coupled pair of racks and cables connected thereto, the torque created by the rotation of the shaft is transmitted to the other shaft. The transmission of torque from one shaft to the other, and the consequential rotation of the other shaft, cause undesired movement of the other coupled pair of racks and cables connected thereto and thus undesired movement of the distal end of the shaft. The transmission of rotational force from one shaft to the other is referred to herein as "cross-coupling".

To overcome this problem, several solutions have been proposed in the prior art. One solution involves minimizing the cross-coupling by providing a mechanism for increasing friction to the rotational motion of the shafts. The additional friction serves to increase the overall resistance to motion but also detrimentally reduces the operational tactile feedback available to the operators of the endoscope. For example, an O-ring may be arranged between the shafts as in U.S. Pat. No. 5,738,631. The presence of the O-ring between the shafts also serves to seal the interior of the endoscope against the entry of contaminants. However, it has been found that torque is transmitted between the pinion shafts by the O-ring and cross-coupling is thus still a problem.

Another solution to the problem is described in Krauter et al. (U.S. Pat. Nos. 5,464,007 and 5,575,755) wherein an O-ring is placed between an inboard end of the outer shaft and a housing frame surrounding the rack and pinion units, and another O-ring is arranged between the inboard end of the inner shaft and the housing frame. The placement of the O-rings purportedly eliminates torque which might be transmitted between the shafts by an O-ring arranged between the pinion shafts (as in U.S. Pat. No. 5,738,631).

Another solution which might prevent the transmission of torque between the shafts in a control mechanism of an endoscope is described in Ouchi et al. (U.S. Pat. No. 4,461,282) wherein a stationary cylinder is fixed to a stationary member of the control mechanism and is interposed between the shafts. A cylindrical pipe is arranged around the cylinder and forms part of a brake operating mechanism for engaging a brake to prevent movement of the knobs. When the braking mechanism is activated, rotation of both knobs is prevented. When the braking mechanism is not activated, torque can be transmitted between the shafts through the stationary cylinder and surrounding pipe. The torque transmission prevention mechanism is thus integrated in combination with the braking mechanism leading to an overall complicated structure. Moreover, it is a drawback that to move the inner knob, a large torque is required in view of the fixing of the stationary cylinder to the stationary member of the control mechanism. That is, since the inner shaft is positioned adjacent (and in apparent contact with) the stationary cylinder, rotation of the inner shaft is difficult because the fixing of the stationary cylinder creates resistance to the rotation of the adjacent inner shaft.

Another drawback in the use of prior art endoscopes occurs when endoscopes are used for transesophageal echocardiographic (TEE) imaging. For TEE imaging, large angular movement of the distal end of the shaft of the endoscope, up to 120° or more, is often necessary. When the endoscope is constructed to provide increased friction to the rotational motion of the shafts in order to obtain large angular movement of the distal end of the shaft of the endoscope, large manual forces must be exerted on the knobs to overcome the resistance and torque generated by the rotation of the shafts relative to their mounting structure.

Thus, the prior art does not describe a control mechanism for an endoscope or similar medical instruments which eliminates the transmission of torque between shafts associated with control knobs and also enables relatively small rotational force to be applied to the knobs to obtain large angular movement of the distal end of the shaft of the endoscope. Similar medical instruments include borescopes and guide tubes and are encompassed herein by the use of the term "endoscope".

It is an object of the present invention to provide a new and improved control mechanism for an endoscope.

It is another object of the present invention to provide a new and improved control mechanism for an endoscope which is particularly useful for TEE imaging in which large angular movement of the distal end of the shaft of the endoscope is possible with minimal rotational force on the knobs.

It is yet another object of the present invention to provide a new and improved control mechanism for an endoscope which eliminates the transmission of torque between shafts associated with control knobs and also enables relatively small rotational force to be applied to the knobs to obtain large angular movement of the distal end of the shaft of the endoscope.

It is still another object of the present invention to provide a new and improved control mechanism for an endoscope which also serves to seal the interior of the endoscope against the entry of contaminants.

In order to achieve these objects and others, a control mechanism for an endoscope in accordance with the invention includes a frame, first and second movement transmission devices for causing adjustment of a distal end of a flexible shaft of the endoscope, first and second independently rotatable control knobs arranged one above the other on the frame, an outer pinion shaft fixed to the first control knob, an inner pinion shaft fixed to the second control knob and an intermediate shaft arranged between the inner and outer shafts. The inner and outer shafts are coaxial with one another. The outer shaft engages with the first movement transmission device such that upon rotation of the first control knob, the outer shaft rotates and the first movement transmission device is actuated. The inner shaft engages with the second movement transmission device such that upon rotation of the second control knob, the inner shaft rotates and the second movement transmission device is actuated.

The intermediate shaft eliminates the transmission of torque between the shafts so that rotation of one of the shafts does not cause rotation of the other shaft. In one embodiment, this objective is achieved by fixing or grounding the intermediate shaft against rotation, possibly by means of a pin attached to the frame and extending into a slot formed in the intermediate shaft. Sealing of the interior of the endoscope is provided by one or more O-rings arranged between the intermediate shaft and each of the inner and outer shafts. If placed between the intermediate shaft and the inner shaft, the O-rings may be placed in a respective circumferential groove formed in the inner shaft in contact with the inner surface of the intermediate shaft. If placed between the intermediate shaft and the outer shaft, the O-rings may be placed in a respective circumferential groove formed in the intermediate shaft in contact with the inner surface of the outer shaft.

In addition to providing a low-resistance rotary seal between the inner or outer shaft and the intermediate shaft, the O-rings transfer torque from the inner or outer shaft to the intermediate shaft, which is grounded against rotation and therefore does not transfer torque to the other shaft. As such, a non-cross-coupling control mechanism is achieved in which the rotation of one control knob and the shaft associated therewith does not have any effect on the other control knob and shaft associated therewith. Undesired actuation of one movement transmission device when the other is being actuated is thus effectively prevented.

To rotatably mount the inner and outer shafts to the frame, ball bearings may be used. One set of ball bearings is arranged between the frame and the outer shaft for rotatably mounting the outer shaft to the frame. Another set is arranged between the outer shaft and the intermediate shaft for enabling rotation of the outer shaft relative to the intermediate shaft. Yet another set is arranged between the intermediate shaft and the inner shaft for enabling rotation of the inner shaft relative to the intermediate shaft.

In one embodiment, the intermediate shaft is axially unrestrained so that it is capable of limited movement in the axial direction (although rotational movement is constrained). The intermediate shaft would thus be capable of moving axially over the O-rings, although such movement is not intentionally imparted to the intermediate shaft. Movement of the intermediate shaft in the axial direction may be limited by the design and construction of the shafts and other parts of the control mechanism. In one embodiment, at least one hard spacer is arranged between a nut fixed to the frame and ball bearings arranged between the outer shaft and the frame to allow floating of the intermediate shaft.

In another embodiment, the ball bearing mounting the outer shaft on the frame is preloaded and instead of hard spacers, a preload spring arranged between the ball bearing and the nut to essentially prevent any axial movement of intermediate shaft by creating a large resistance to such axial movement.

The invention, together with further objects and advantages hereof, may best be understood by reference to the following description taken in conjunction with the accompanying drawings, wherein like reference numerals identify like elements and wherein.

Figure 1:
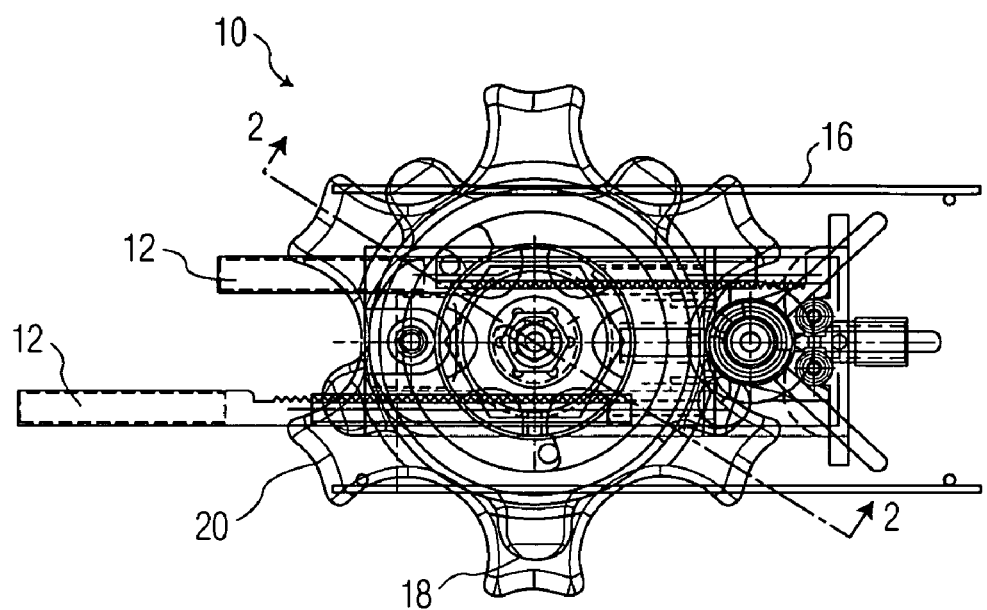
FIG. 1 is a top view of a control mechanism for an endoscope in accordance with the invention.

Referring to the accompanying drawings wherein like reference numerals refer to the same or similar elements, FIG. 1 shows a control mechanism 10 for an endoscope in accordance with the invention including a first pair of racks 12 arranged in a common plane and a second pair of racks 14 arranged in another common plane. The control mechanism 10 is arranged in connection with a control head or control handle of the endoscope, the housing of which is not shown. The control head is connected to a flexible shaft or gastroscope (not shown) which is inserted into the body cavity for examination of the internal organs or other internal structures.

As known in the art, the racks 12,14 are each coupled to a cable (not shown) that actuates endoscopic flexible links arranged at a distal end of the shaft so that movement of the racks 12,14 causes movement of the coupled cables and thus movement of the distal end of the shaft of the endoscope. Instead of racks 12,14, other movement transmission devices for converting rotational motion into motion of a distal end of the shaft of the endoscope, including those known in the art of endoscopy such as cable and pulleys, may be used.

The control mechanism 10 includes a housing or frame 16, a first, outer control knob 18 and a second, inner control knob 20 arranged below and concentric with the first control knob 18. The control knobs 18,20 are mounted to be independently rotatable, i.e., rotation of one control knob does not cause rotation of the other control knob.

The first control knob 18 is connected to a first rotatable pinion shaft 22 which includes a shaft portion 24 which extends through an opening in the second control knob 20 and a pinion portion 26 which engages with the lowermost pair of racks 14. Rotation of the first control knob 18 causes rotation of the first pinion shaft 22 which in turn causes movement of the racks 14 and thus movement of the distal end of the flexible shaft of the endoscope in one plane, for example, in a horizontal plane with left or right movement.

The second control knob 20 is connected to a second rotatable pinion shaft 28 which includes a tubular shaft portion 30 which extends around and is coaxial with the shaft portion 24 of the first pinion shaft 22 and a pinion portion 32 which engages with the uppermost pair of racks 12. Rotation of the second control knob 20 causes rotation of the second pinion shaft 28 which in turn causes movement of the racks 12 and thus movement of the distal end of the flexible shaft of the endoscope in a direction different from the direction of movement caused by movement of the racks 14, usually movement in a plane perpendicular to the direction of movement caused by the movement of the racks 14, for example, in a vertical plane with up and down movement.

In view of the positioning of the shaft portion 24 of the first pinion shaft 22 inside the shaft portion 30 of the second pinion shaft 28, the first pinion shaft 22 would be considered an inner shaft (and will be referred to as such below) with the first control knob 18 being an inner or upper control knob whereas the second pinion shaft 28 would be an outer shaft (and will be referred to as such below) with the second control knob 20 being an outer or lower control knob. This is generally conventional in the art.

In accordance with the invention, an intermediate shaft 34 is arranged between the inner and outer pinion shafts 22,28 to reduce and ideally prevent the transmission of torque between the inner and outer pinion shafts 22,28. That is, in the prior art, O-rings are usually used to seal a space between inner and outer, coaxial pinion shafts and are in contact with both the inner and outer shafts so that torque is transmitted upon rotation of one pinion shaft to the other pinion shaft via the O-rings thereby causing undesired movement of the distal end of the endoscope.

The invention eliminates the possibility of transmitting torque generated upon rotation of one pinion shaft to another pinion shaft via O-rings by interposing the rotationally grounded intermediate shaft 34 between the inner and outer pinion shafts 22,28 and providing O-rings 42,46 between the intermediate shaft 34 and the inner and outer shafts 22,28. In view of the presence of the intermediate shaft 34, rotation of one pinion shaft 22,28 will therefore not result in rotation of the other pinion shaft 22,28 so that undesirable movement of the racks 12,14 is prevented.

The intermediate shaft 34 has a tubular portion extending over and coaxial with the shaft portion 24 of the inner shaft 22 and a detent ring 36. The tubular portion extends entirely through and is coaxial with the shaft portion 30 of the outer pinion shaft 28. The detent ring 36 at one axial end of the intermediate shaft 32 is arranged between a flange 38 of the inner pinion shaft 22 and the outer pinion shaft 28 and the opposite axial end of the intermediate shaft 34 is arranged in a recess 40 of the second control knob 20.

Figure 3:
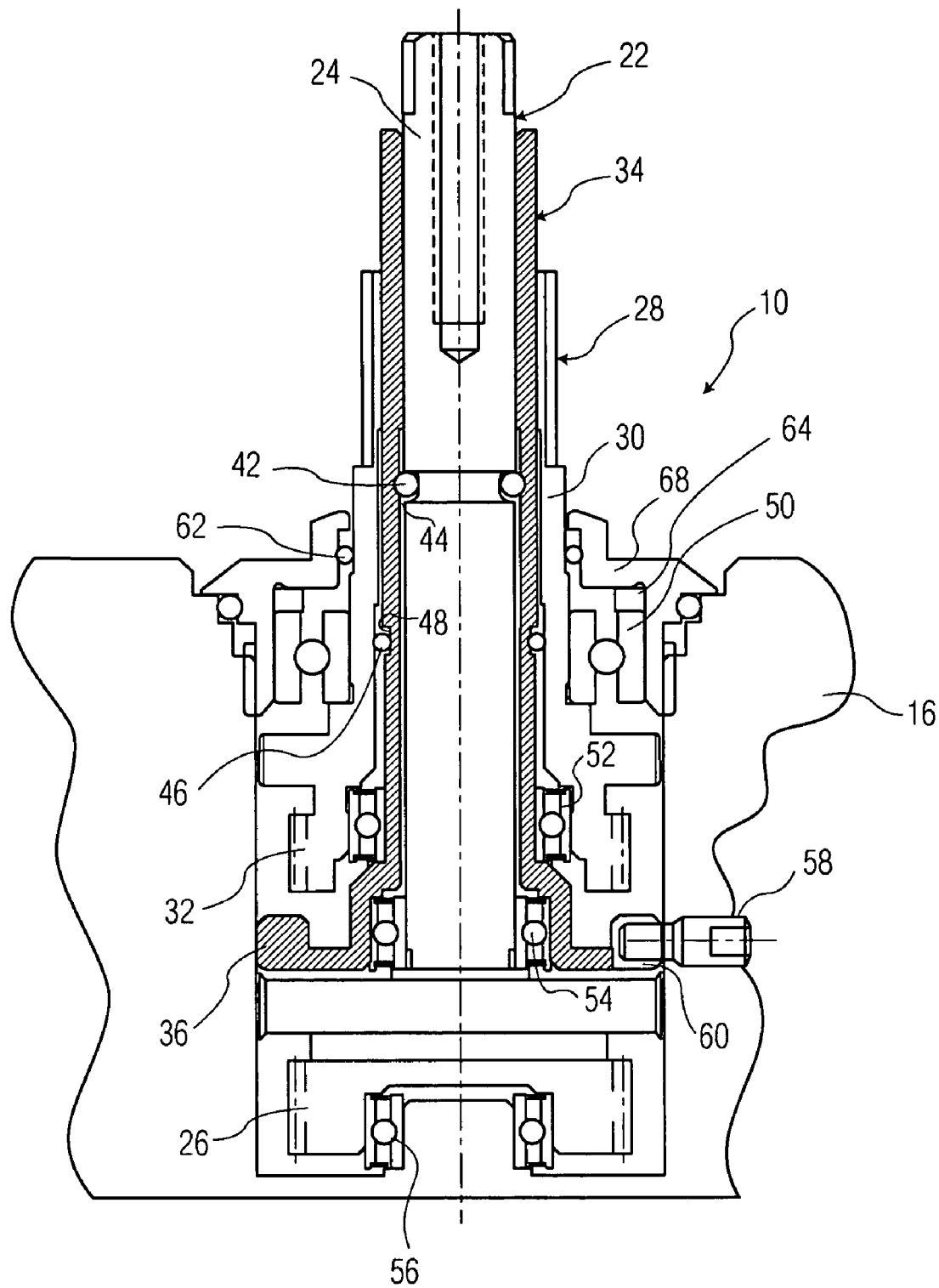
FIG. 3 is an enlarged view of a part of the control mechanism shown in FIG. 1.
Figure 4:
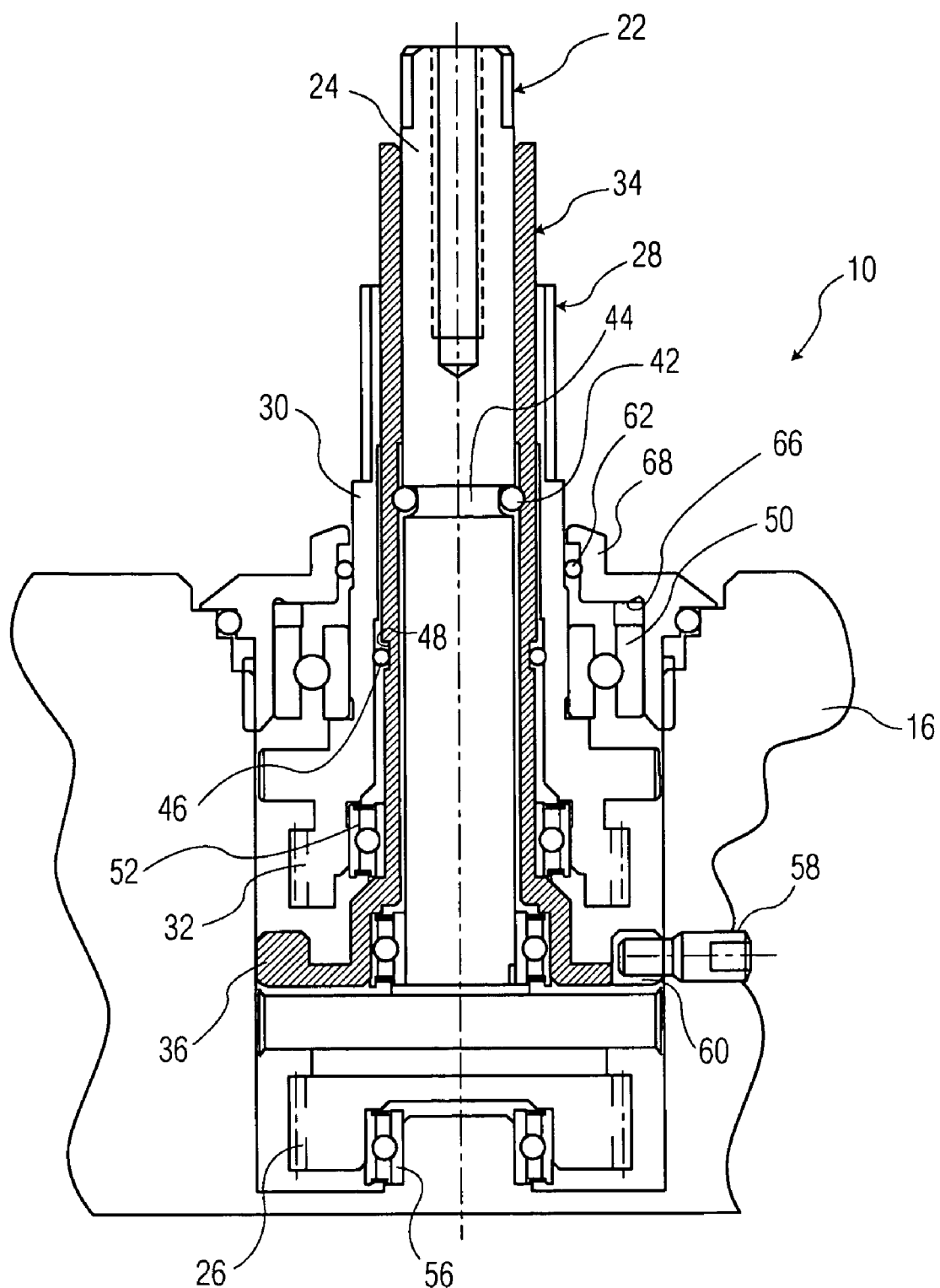
FIG. 4 is an enlarged view of part of another embodiment of the control mechanism in accordance with the invention.

Grounding of the intermediate shaft 34 against rotation may be provided by a pin 58 mounted to the frame 16 (see FIGS. 3 and 4). The pin 58 fits into a slot 60 formed in the intermediate shaft 34 and is screwed through the frame 16. The slot 60 is oriented to constrain rotation while allowing axial movement of the intermediate shaft 34. Instead of the pin 58, other mechanisms for grounding or fixing the intermediate shaft 34 against rotation can be used.

Figure 2:
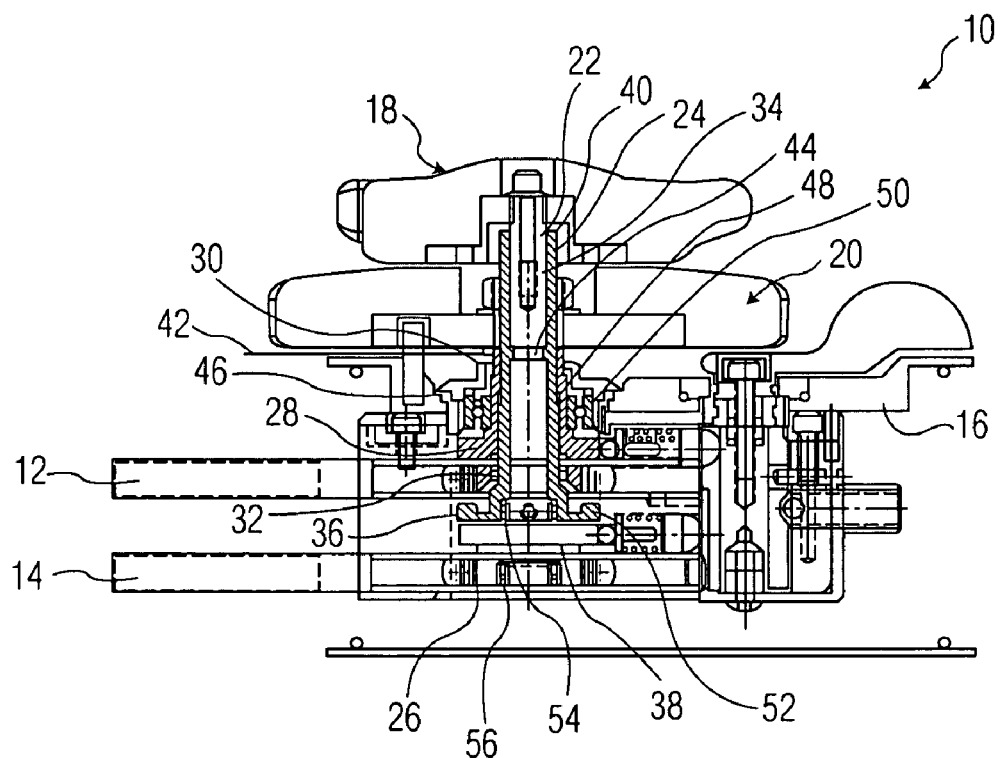
FIG. 2 is a cross-sectional view of the control mechanism shown in FIG. 1 taken along the line 2-2.

The small stretched O-rings 42,46 reduce the magnitude of the torque required for the control mechanism 10 while still providing a seal of the interior of the endoscope. O-ring 42 is arranged in a circumferential groove 44 formed on the outer surface of the inner pinion shaft 22 and is in contact with an inner surface of the intermediate shaft 34. The O-ring 42 provides a low-resistance rotary seal between the inner pinion shaft 22 and the intermediate shaft 34. O-ring 46 is arranged in a circumferential groove 48 formed on the outer surface of the intermediate shaft 34 and is in contact with an inner surface of the outer pinion shaft 28 (see FIG. 2). The O-ring 46 provides a low-resistance rotary seal between the outer pinion shaft 28 and the intermediate shaft 34.

When the second control knob 20 is rotated causing rotation of the associated outer pinion shaft 28, the rotation of the outer pinion shaft 28 relative to the intermediate shaft 34 causes torque to be transmitted to the O-ring 46 and applied via the O-ring 46 to the intermediate shaft 34. However, torque is not transmitted to the inner pinion shaft 22 so that cross-coupling between the manual rotation of the second control knob 20 and rotation of the first control knob 18 and associated inner pinion shaft 22 is prevented. Similarly, when the first control knob 18 is rotated causing rotation of the associated inner pinion shaft 22, the rotation of the inner pinion shaft 22 relative to the intermediate shaft 34 causes torque to be transmitted to the O-ring 42 and applied via the O-ring 42 to the intermediate shaft 34. However, torque is not transmitted to the outer pinion shaft 28 so that cross-coupling between the manual rotation of the first control knob 18 and rotation of the second control knob 20 and associated outer pinion shaft 28 is prevented.

A "non-cross-coupled" control mechanism, a control mechanism in which rotation of one shaft and associated control knob does not cause rotation of the other shaft and associated control knob through the transmission of torque between the shafts, is thus achieved. As a result of the non-cross-coupling provided by the control mechanism in accordance with the invention, there is no interaction between the control knobs 18,20, i.e., one control knob does not interact with the other, and thus undesired movement of the distal end of the endoscope is prevented.

The presence of the O-rings 42,46 does not create a large resistance to rotation of the inner or outer pinion shafts 22,28 so that a relatively low torque is required to overcome the sealing forces provided by the O-rings 42,46 and turn the control knobs 18,20. In the preferred embodiment, the O-rings 42,46 have a diameter of about 0.05 inches and are stretched over the inner pinion shaft 22 and the intermediate shaft 34 to about 60% to 70% of the original diameter. However, larger or smaller O-rings can be used. Stretching the O-rings 42,46 reduces the part-to-part molded diameter variations so that variations in the original diameter of the O-rings 42,46 do not adversely affect the construction of the control mechanism 10.

The control mechanism 10 further includes low friction, optionally pre-loaded, ball bearings 50 arranged between the frame 16 and the outer pinion shaft 28 for rotatably mounting the outer pinion shaft 28 on the frame 16. Ball bearings 52 are also arranged between the outer pinion shaft 28 and the intermediate shaft 34 for enabling rotation of the outer pinion shaft 28 relative to the intermediate shaft 34. The outer pinion shaft 28 is fixed to the ball bearings 50,52. Additional ball bearings 54 are arranged between the intermediate shaft 34 and the inner pinion shaft 22 for enabling rotation of the inner pinion shaft 22 relative to the intermediate shaft 34. Ball bearings 56 are arranged between the inner pinion shaft 22 and the frame 16 for rotatably mounting the inner pinion shaft 22 on the frame 16. The inner pinion shaft 22 is fixed to the ball bearings 54,56. Instead of ball bearings 50,52,54,56 other devices which enable relative rotation of coaxial structures may be used.

In one embodiment shown in FIG. 3, the intermediate shaft 34 is grounded against rotation but is not axially constrained so that axial movement of the intermediate shaft 34 is possible, i.e., the intermediate shaft 34 can float in the axial direction. The intermediate shaft 34 is shimmed to reduce its floating to virtually zero. In this regard, one or more hard spacers 64 are provided between the ball bearings 50 and the frame 16 to achieve a minimal endplay, i.e., allow the axial movement of the intermediate shaft 34. The spacers 64 preferably have a size to provide for an allowable endplay of from about 0.001 inches to 0.010 inches, although smaller or larger are foreseen. A nut 68 restrains the hard spacers 64.

An additional O-ring 62 may be stretched over the outer pinion shaft 28 to provide a seal between the outer pinion shaft 28 and the nut 68 fixed to the frame 16. In the embodiment shown in FIG. 4, instead of a floating intermediate shaft, a preloaded intermediate shaft is provided. In this embodiment, the hard spacers 64 are replaced by a preload spring 66, such as a wavy washer spring, which preloads the outer race of bearing 50 to eliminate any endplay. Thus, while the intermediate shaft 34 does not float, it is not axially grounded.

Although illustrative embodiments of the present invention have been described herein with reference to the accompanying drawings, it is to be understood that the invention is not limited to these precise embodiments, and that various other changes and modifications may be effected therein by one of ordinary skill in the art without departing from the scope or spirit of the invention. For example, although the control mechanism in accordance with the invention is described for use with an endoscope, it is contemplated that the control mechanism can be used in other medical and non-medical devices in which movement transmission devices are controlled by control knobs having coaxial shafts.

The invention claimed is:

1. A control mechanism for an endoscope having a handle, and a flexible shaft extending from the handle and having a distal or operative end which is inserted into a body through a body cavity, the distal end of the shaft including an image receiving sensor, the control mechanism comprising:
    a frame;
    first and second movement transmission devices for causing adjustment of a distal end of the flexible shaft;
    a first control knob;
    a first rotatable pinion shaft rotatably mounted on said frame and fixed to said first control knob, said first pinion shaft engaging with said first movement transmission device such that upon rotation of said first control knob, said first pinion shaft rotates and said first movement transmission device is actuated;
    a second control knob rotatable independent of said first control knob;
    a second rotatable pinion shaft fixed to said second control knob and coaxial with said first pinion shaft, said second pinion shaft engaging with said second movement transmission device such that upon rotation of said second control knob, said second pinion shaft rotates and said second movement transmission device is actuated;
    an intermediate shaft arranged at least partially inside of said second pinion shaft and at least partially around said first pinion shaft, said intermediate shaft being arranged to reduce transmission of torque between said first and second pinion shafts such that rotation of one of said first and second pinion shafts does not cause rotation of the other of said first and second pinion shafts, said intermediate shaft being axially unrestrained such that movement of said intermediate shaft in an axial direction is possible;
    first ball bearings arranged between said intermediate shaft and one of said first and second pinion shafts for enabling rotation of said one of said first and second pinion shafts relative to said intermediate shaft.

2. The control mechanism of claim 1, further comprising at least one O-ring arranged on said first pinion shaft and in contact with said intermediate shaft such that torque transmitted by said first pinion shaft to said at least one O-ring is applied to said intermediate shaft.

3. The control mechanism of claim 2, wherein said first pinion shaft includes at least one circumferential groove for receiving a respective one of said at least one O-ring.

4. The control mechanism of claim 2, wherein said at least one O-ring is arranged to provide a rotary seal between said first pinion shaft and said intermediate shaft.

5. The control mechanism of claim 1, further comprising at least one O-ring arranged on said intermediate shaft and in contact with said second pinion shaft such that torque transmitted by said second pinion shaft to said at least one O-ring is applied to said intermediate shaft.

6. The control mechanism of claim 5, wherein said intermediate shaft includes at least one circumferential groove for receiving a respective one of said at least one O-ring.

7. The control mechanism of claim 5, wherein said at least one O-ring is arranged to provide a rotary seal between said second pinion shaft and said intermediate shaft.

8. The control mechanism of claim 1, further comprising a first O-ring arranged on said first pinion shaft and in contact with said intermediate shaft such that torque transmitted by said first pinion shaft to said at least one O-ring is applied to said intermediate shaft and a second O-ring arranged on said intermediate shaft and in contact with said second pinion shaft such that torque transmitted by said second pinion shaft to said at least one O-ring is applied to said intermediate shaft.

9. The control mechanism of claim 1, further comprising fixing means for fixing said intermediate shaft against rotation.

10. The control mechanism of claim 9, wherein said fixing means comprise a pin attached to said frame and extending into a slot formed in said intermediate shaft.

11. The control mechanism of claim 1, further comprising a nut fixed to said frame, additional ball bearings arranged between said second pinion shaft and said frame for rotatably mounting said second pinion shaft to said frame and at least one hard spacer arranged between said nut and said additional ball bearings to allow floating of said intermediate shaft.

12. The control mechanism of claim 1, further comprising a nut fixed to said frame, additional ball bearings arranged between said second pinion shaft and said frame for rotatably mounting said second pinion shaft to said frame and a preload spring arranged between said nut and said additional ball bearings, said additional ball bearings being preloaded.

13. A control and sealing mechanism for an endoscope having a handle, and a flexible shaft extending from the handle and having a distal or operative end which is inserted into a body through a body cavity, the distal end of the shaft including an image receiving sensor, the control and sealing mechanism comprising:
    a frame;
    first and second movement transmission devices for causing adjustment of a distal end of the flexible shaft;
    a first control knob;
    a first rotatable pinion shaft rotatably mounted on said frame and fixed to said first control knob, said first pinion shaft engaging with said first movement transmission device such that upon rotation of said first control knob, said first pinion shaft rotates and said first movement transmission device is actuated;

a second control knob rotatable independent of said first control knob;

a second rotatable pinion shaft fixed to said second control knob and coaxial with said first pinion shaft, said second pinion shaft engaging with said second movement transmission device such that upon rotation of said second control knob, said second pinion shaft rotates and said second movement transmission device is actuated;

an intermediate shaft arranged at least partially inside of said second pinion shaft and at least partially around said first pinion shaft, said intermediate shaft being axially unrestrained such that movement of said intermediate shaft in an axial direction is possible;

at least one O-ring arranged in contact with said intermediate shaft and one of said first and second pinion shafts such that torque transmitted by said first or second pinion shaft to said at least one O-ring is applied to said intermediate shaft and transmission of torque between said first and second pinion shafts is reduced, said at least one O-ring being arranged to provide a rotary seal between said intermediate shaft and said one of said first and second pinion shafts; and first ball bearings arranged between said intermediate shaft and one of said first and second pinion shafts for enabling rotation of said one of said first and second pinion shafts relative to said intermediate shaft.

14. The mechanism of claim 13, wherein said at least one O-ring is arranged on said intermediate shaft and in contact with said second pinion shaft such that torque transmitted by said second pinion shaft to said at least one O-ring is applied to said intermediate shaft.

15. The mechanism of claim 14, wherein said intermediate shaft includes at least one circumferential groove for receiving a respective one of said at least one O-ring.

16. The mechanism of claim 13, wherein said at least one O-ring is arranged on and in contact with said first pinion shaft such that torque transmitted by said first pinion shaft to said at least one O-ring is applied to said intermediate shaft.

17. The mechanism of claim 16, wherein said first pinion shaft includes at least one circumferential groove for receiving a respective one of said at least one O-ring.

18. The mechanism of claim 13, wherein said at least one O-ring comprises a first O-ring arranged on said intermediate shaft and in contact with said second pinion shaft such that torque transmitted by said second pinion shaft to said at least one O-ring is applied to said intermediate shaft, and a second O-ring arranged on and in contact with said first pinion shaft such that torque transmitted by said first pinion shaft to said at least one O-ring is applied to said intermediate shaft.

19. The mechanism of claim 13, further comprising a nut fixed to said frame, additional ball bearings arranged between said second pinion shaft and said frame for rotatably mounting said second pinion shaft to said frame and at least one hard spacer arranged between said nut and said additional ball bearings to allow floating of said intermediate shaft.

20. The mechanism of claim 13, further comprising a nut fixed to said frame, additional ball bearings arranged between said second pinion shaft and said frame for rotatably mounting said second pinion shaft to said frame and a preload spring arranged between said nut and said additional ball bearings, said additional ball bearings being preloaded.

21. The control mechanism of claim 1, further comprising second ball bearings arranged between said intermediate shaft and another one of said first and second pinion shafts for enabling rotation of said other one of said first and second pinion shafts relative to said intermediate shaft.

* * * * *